(12) United States Patent  
VanderNoot et al.

(10) Patent No.: US 9,322,014 B1  
(45) Date of Patent: Apr. 26, 2016

(54) MULTIPLEXED MICROFLUIDIC APPROACH FOR NUCLEIC ACID ENRICHMENT

(71) Applicant: Sandia Corporation, Albuquerque, NM (US)

(72) Inventors: Victoria A. VanderNoot, Pleasanton, CA (US); Stanley Alan Langevin, Seattle, WA (US); Zachary Bent, Dublin, CA (US); Ronald F. Renzi, Tracy, CA (US); Scott M. Ferko, Livermore, CA (US); James L. Van De Vreugde, Livermore, CA (US); Todd Lane, Livermore, CA (US); Kamlesh Patel, Dulbin, CA (US); Steven Branda, Livermore, CA (US)

(73) Assignee: Sandia Corporation, Albuquerque, NM (US)

( * ) Notice: Subject to any disclaimer, the term of this patent is extended or adjusted under 35 U.S.C. 154(b) by 0 days.

(21) Appl. No.: 14/084,937

(22) Filed: Nov. 20, 2013

Related U.S. Application Data

(60) Provisional application No. 61/730,820, filed on Nov. 28, 2012.

(51) Int. Cl.  
*C12Q 1/68* (2006.01)  
*G01N 30/08* (2006.01)  
(Continued)

(52) U.S. Cl.  
CPC ............... *C12N 15/101* (2013.01); *C12Q 1/68* (2013.01); *C12Q 1/6806* (2013.01); *G01N 30/04* (2013.01);  
(Continued)

(58) Field of Classification Search  
CPC ....... G01N 30/02; G01N 30/04; G01N 30/08; G01N 30/18; G01N 30/20; G01N 30/6034; G01N 30/6043; G01N 30/6091; G01N 30/6095; G01N 30/66; G01N 30/80; G01N 30/82; C12Q 1/68; C12Q 1/6806; C12Q 1/6811; Y10T 436/11; Y10T 436/143333; Y10T 436/25; Y10T 436/25125; Y10T 436/25375; Y10T 436/255; Y10T 436/2575  
USPC ............. 436/43, 94, 147, 149, 150, 161, 174, 436/175, 177, 178, 180; 435/6.1, 287.1, 435/287.2, 288.6; 422/63, 68.1, 70, 82.01, 422/82.02, 82.12, 527; 210/656, 198.2  
See application file for complete search history.

(56) References Cited

U.S. PATENT DOCUMENTS 5,208,160 A * 5/1993 Kikyotani et al. ............ 435/270  
5,482,845 A   1/1996 Soares et al.  
(Continued)

OTHER PUBLICATIONS

Vandernoot et al. Biotechniques, vol. 53, No. 6, Dec. 2012, pp. 373-380.*

(Continued)

*Primary Examiner* — Maureen Wallenhorst  
(74) *Attorney, Agent, or Firm* — Helen S. Baca; Dorsey & Whitney, LLP

(57) ABSTRACT

A system for enhancing a nucleic acid sample may include a one pump, a denaturing chamber; a microfluidic hydroxyapatite chromatography device configured for performing hydroxyapatite chromatography on the nucleic acid sample, a sample collector, and tubing connecting the pump with the denaturing chamber, the hydroxyapatite chromatography device and the sample collector such that the pump may be used to move the nucleic acid sample from the denaturing chamber to the hydroxyapatite chromatography device and then to the sample collector.

29 Claims, 12 Drawing Sheets

(51) Int. Cl.
  *G01N 30/66* (2006.01)
  *G01N 30/82* (2006.01)
  *C12N 15/10* (2006.01)
  *G01N 30/60* (2006.01)
  *G01N 30/04* (2006.01)

(52) U.S. Cl.
  CPC ............ *G01N 30/08* (2013.01); *G01N 30/6043* (2013.01); *C12Q 1/6811* (2013.01); *G01N 30/66* (2013.01); *G01N 30/82* (2013.01); *Y10T 436/143333* (2015.01); *Y10T 436/25* (2015.01); *Y10T 436/255* (2015.01); *Y10T 436/2575* (2015.01)

(56) References Cited

U.S. PATENT DOCUMENTS

| | | | |
|---|---|---|---|
| 5,702,898 | A | 12/1997 | Bonaldo et al. |
| 6,444,426 | B1 | 9/2002 | Short et al. |
| 7,049,065 | B2 | 5/2006 | Hayashizaki |
| 7,452,507 | B2 | 11/2008 | Renzi et al. |
| 2002/0164634 | A1* | 11/2002 | Patil et al. ............ 435/6 |
| 2004/0241698 | A1* | 12/2004 | Hauer et al. ........... 435/6 |
| 2008/0199862 | A1* | 8/2008 | Gu et al. ............... 435/6 |
| 2013/0248451 | A1* | 9/2013 | Hall et al. ............ 210/659 |

OTHER PUBLICATIONS

Antoniou, et al., "Gene expression in mouse oocytes by RNA-Seq", Methods in Molecular Biology; vol. 825, 2012, 237-251.
Bartram, et al., "Generation of Multimillion-Sequence 16S rRNA Gene Libraries from Complex Microbial Communities by Assembling Paired-End Illumina Reads", Applied and Environmental Microbiology; vol. 77, No. 11, Jun. 2011, 3846-3852.
Chen, et al., "Comparative Analysis of Human Protein-Coding and Noncoding RNAs between Brain and 10 Mixed Cell Lines by RNA-Seq", PLoS One; vol. 6, Issue 1, Nov. 2011.
Chirica, et al., "Size exclusion chromatography of microliter volumes for online use in low-pressure microfluidic systems", Analytical Chemistry; vol. 78, 2006, 5362-5368.
Cosart, et al., "Exome-wide DNA capture and next generation sequencing in domestic and wild species", BMC Genomics; vol. 12, Jul. 5, 2011, 347-355.
Costa, et al., "Uncovering the Complexity of Transcriptomes with RNA-Seq", Journal of Biomedicine and Biotechnology; Article ID: 853916, 2010.
Gijavanekar, et al., "Rare target enrichment for ultrasensitive PCR detection using cot-rehybridization and duplex-specific nuclease", Analytical Biochemistry; vol. 421, 2012, 81-85.
Gil, et al., "Automated analysis of mouse serum peptidome using restricted access media and nonoliquid chromatography-tandem mass spectrometry", Journal of Chromatography B; vol. 879, 2011, 1112-1120.
Ko, et al., "An 'equalized cDNA library' by the reassociation of short double-stranded cDNAs", Nucleic Acids Research; vol. 18, No. 19, Jul. 1990, 5705-5711.
Ozsolak, et al., "RNA sequencing: advances, challenges and opportunities", Nature Reviews Genetics; vol. 12, May 1, 2011, 87-98.
Peterson, et al., "Integration of Cot Analysis, DNA Cloning, and High-Throughput Sequencing Facilitates Genome Characterization and Gene Discover", Genome Research; vol. 12, 2002, 795-807.
Pinto, et al., "Application of RNA-seq to reveal the transcript profile in bacteria", Genetics and Molecular Research; vol. 10(3), 2011, 1707-1718.
Puzyrev, et al., "A normalized cDNA library from human erythroleukemia cells", Journal of Molecular Biology; vol. 29, 1995, 97-103.
Roberts, et al., "Identification of novel transcripts in annotated genomes using RNA-Seq", Bioinformatics; vol. 27, No. 17, 2011, 2325-2329.
Shcheglov, et al., "Normalization of cDNA Libraries", Nucleic Acids Hybridization, 2007, 97-124.
Soares, et al., "Construction and characterization of a normalized cDNA library", Proceedings of the National Academy of Sciences; vol. 91, Sep. 1994, 9228-9232.
Stachowiak, et al., "Autonomous microfluidic sample preparation system for protein profile-based detection of aerosolized bacterial cells and spores", Analytical Chemistry; vol. 79, 2007, 5763-5770.
Andrews-Pfannkoch C et al., "Hydroxyapatite-mediated separation of double-stranded DNA, single-stranded DNA, and RNA genomes from natural viral assemblages," *Appl. Environ. Microbiol.* Aug. 2010;76(15):5039-45.
Bent ZW et al., "Enriching pathogen transcripts from infected samples: a capture-based approach to enhanced host-pathogen RNA sequencing," *Anal. Biochem.* Jul. 1, 2013;438(1):90-6.
Bent ZW et al., "Use of a capture-based pathogen transcript enrichment strategy for RNA-Seq analysis of the Francisella tularensis LVS transcriptome during infection of murine macrophages," *PLoS One* Oct. 14, 2013;8(10):e77834 (12 pp.).
Bogdanova EA et al., "Normalizing cDNA libraries," *Curr. Protoc. Mol. Biol.* Apr. 2010;91:5.12.1-5.12.27.
Branda SS et al., "Characterization of pathogens in clinical specimens via suppression of host background for efficient second generation sequencing analyses," *20th International Conference on Biodetection Technologies 2012, Technological Advances in Detection & Identification of Biological Threats*, held on Jun. 28-29, 2012 in Washington, DC (27 pp.).
Britten RJ et al., "Repeated sequences in DNA," *Science* Apr. 1968;161(3841):529-40.
Fadrosh DW et al., "Separation of single-stranded DNA, double-stranded DNA and RNA from an environmental viral community using hydroxyapatite chromatography," *J. Vis. Exp.* Sep. 29, 2011;(55). pii: 3146 (5 pp.).
Freitag R et al., "Isolation and purification of recombinant proteins, antibodies and plasmid DNA with hydroxyapatite chromatography," *Biotechnol. J.* Jan. 2012;7(1):90-102.
Fruetel JA et al., "Microchip separations of protein biotoxins using an integrated hand-held device," *Electrophoresis* Mar. 2005;26(6):1144-54.
Levin JZ et al., "Comprehensive comparative analysis of strand-specific RNA sequencing methods," *Nat. Methods* Sep. 2010;7(9):709-15.
Lo L et al., "3640 unique EST clusters from the medaka testis and their potential use for identifying conserved testicular gene expression in fish and mammals," *PLoS One* 2008;3(12):e3915 (7 pp.).
Parimoo S et al., "cDNA selection: Efficient PCR approach for the selection of cDNAs encoded in large chromosomal DNA fragments," *Proc. Nat'l Acad. Sci. USA* Nov. 1991;88(21):9623-7.
Patanjali SR et al., "Construction of a uniform-abundance (normalized) cDNA library," *Proc. Nat'l Acad. Sci. USA* Mar. 1, 1991;88(5):1943-7.
Renzi RF et al., "Hand-held microanalytical instrument for chip-based electrophoretic separations of proteins," *Anal. Chem.* Jan. 15, 2005;77(2):435-41.
Revilla-López G et al., "Modeling biominerals formed by apatites and DNA," *Biointerphases* Dec. 2013;8(1):10 (15 pp.).
Timblin C et al., "Application for PCR technology to subtractive cDNA cloning: identification of genes expressed specifically in murine plasmacytoma cells," *Nucleic Acids Res.* Mar. 25, 1990;18(6):1587-93.
Vandernoot V et al., "On-line monitoring system for chemical warfare agents using automated capillary micellar electrokinetic chromatography," *J. Chromatogr. A* Aug. 3, 2012;1249:233-40.
Vandernoot VA et al., "cDNA normalization by hydroxyapatite chromatography to enrich transcriptome diversity in RNA-seq applications," *Biotechniques* Dec. 2012;53(6):373-80.
VanderNoot VA et al., "Development of an integrated microfluidic instrument for unattended water-monitoring applications," *Electrophoresis* Aug. 2010;31(15):2632-4.

* cited by examiner

US 9,322,014 B1

MULTIPLEXED MICROFLUIDIC APPROACH FOR NUCLEIC ACID ENRICHMENT

CROSS-REFERENCE TO RELATED APPLICATION(S)

This application claims the benefit of the earlier filing date of U.S. Provisional Patent Application Ser. No. 61/730,820, entitled "Multiplexed Microfluidic Approach for Nucleic Acid Enrichment," filed Nov. 28, 2012, which application is hereby incorporated by reference in its entirety for any purpose.

STATEMENT OF GOVERNMENT INTEREST

This invention was made with Government support under contract no. DE-AC04-94AL85000 awarded by the U.S. Department of Energy to Sandia Corporation. The Government has certain rights in the invention.

TECHNICAL FIELD

Embodiments of the invention relate generally to microfluidic systems and methods for nucleic acid signal enrichment.

BACKGROUND

Second generation sequencing (SGS) has revolutionized whole genome sequencing and transcriptome analysis of many organisms. In particular, sequencing of cDNA made from cellular RNA (RNA-Seq) enables RNA expression profiling with high dynamic range and genome coverage. RNA-Seq has expanded our knowledge of non-coding transcripts and led to discoveries of novel alternative splicing of RNA in various eukaryotic cell types. The primary component of eukaryotic total RNA is ribosomal RNA (rRNA), with all other coding, noncoding, and small RNAs representing less than 15% of the total RNA population. High abundance of rRNA-derived sequences in cDNA libraries diminishes the utility of SGS RNA-Seq for functional genomics studies, because only a small fraction of reads are from sequences of interest. In this context, cDNA library preparation techniques that efficiently remove highly abundant rRNA-derived sequence populations prior to sequencing are highly desirable.

A common method for excluding rRNA is to select for mRNAs that contain long polyadenylated tails, for example by using polythymidine primers in cDNA construction protocols. This approach, while highly effective in removing rRNA, also depletes all non-polyadenylated host transcripts, such as non-coding RNAs that regulate eukaryotic cellular function and viral and prokaryotic microbial sequences present in many complex sample types. Alternative ribosomal RNA removal protocols such as ribosomal oligonucleotide mediated capture techniques (e.g., Ribominus™ and RiboZero™) are species-specific and require extensive ribosomal sequence data for probe design. Both techniques are multistep procedures, during which RNA can degrade, and both require large amounts of starting material (1-10 µg of total RNA), limiting the experimental design and sample-types for which they are practical.

Hydroxyapatite Chromatography-Based Normalization

An alternative to excluding rRNA sequences from cDNA preparation is to apply techniques, variously called cDNA normalization or $C_0t$ filtration, that remove highly abundant sequences from DNA libraries. FIG. 1 illustrates the basic process of DNA normalization. The process begins with a starting DNA population 10 (or "sample"). In normalization, double stranded DNA populations are first denatured at an elevated temperature 12, and then allowed to re-anneal (or "rehybridize") 14, typically at a reduced temperature. Highly abundant sequences hybridize at higher rates (proportional to the square of their concentration) and, if the re-annealing reaction is stopped at a suitable time (e.g. 4-24 hours), the highly abundant sequences comprise the majority of double-stranded species. The next step in the process is to separate double-stranded DNA (dsDNA) 16 and single-stranded DNA (ssDNA) 18. If the two can be separated, the representation of the highest abundance species in the resulting ssDNA fraction can be significantly reduced.

HAC has not yet gained widespread usage in the normalization arena compared to the duplex-specific thermostable nuclease (DSN) approach for RNA-Seq applications, however, possibly as a result of perceived disadvantages. These disadvantages include labor intensiveness, unacceptably high starting material requirements, and poor reproducibility.

Capture Based Nucleic Acid Enrichment/Suppression

Another alternative approach for nucleic acid signal enrichment/suppression is based on the selective capture of unwanted sequences. In capture mode, the sample is also denatured and then allowed to anneal in the presence of excess biotinylated probes generated against the highly abundant species. The probes and any nucleic acids bound to them are then captured in a streptavidin chromatography column, and the resulting sample flowing through the column is then depleted with respect to the high abundance species. Commercially available kits enable capture-based enrichment of libraries for the human exome. However, these kits are not versatile; they have very limited utility outside of human SNP detection.

These two techniques—HAC and capture-based enrichment—have been shown to be highly effective, but both are generally very time and labor intensive, require unacceptably large amounts of starting material (sample), and have poor reproducibility. Therefore, it would be desirable to have new systems and methods for enriching nucleic acid samples. Ideally, such systems and methods would be less time and labor intensive, would work with smaller sample sizes than required by current methods, and would be highly reproducible.

DETAILED DESCRIPTION

Figure 1:
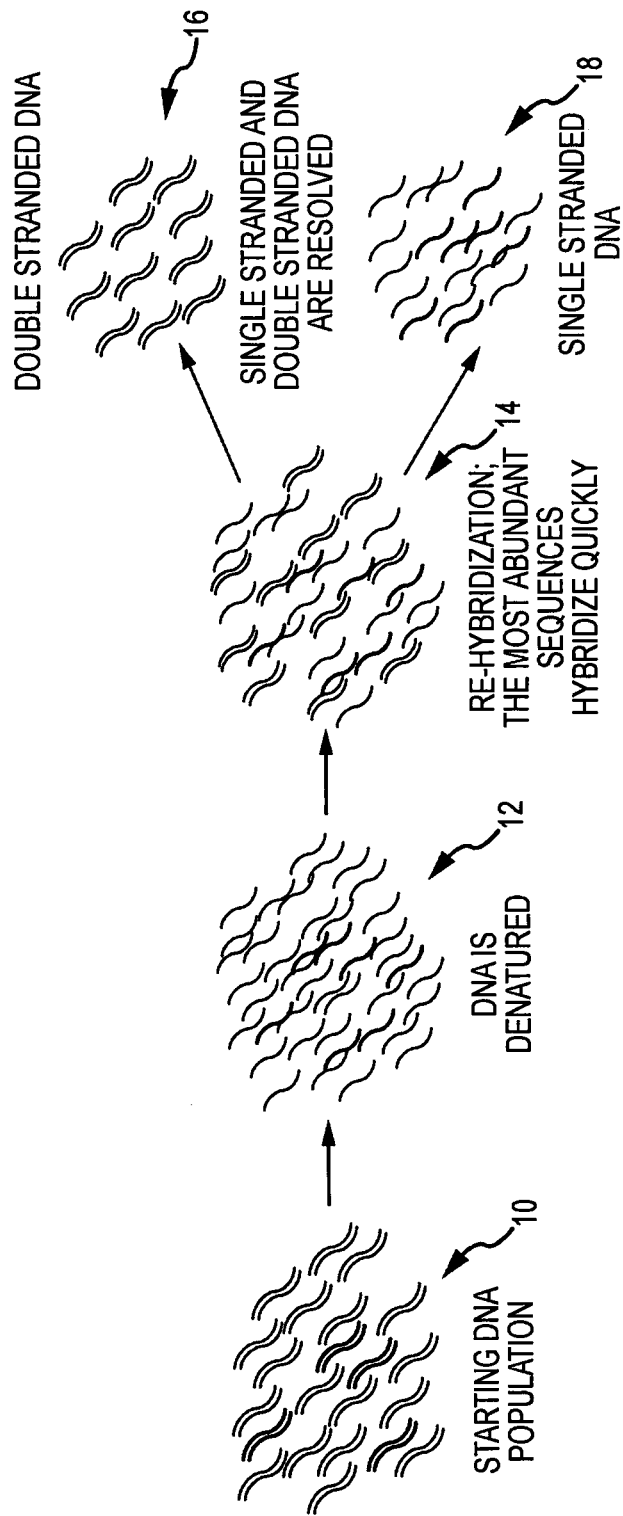
FIG. 1 is a diagram illustrating the basic steps in DNA normalization process.

Certain details are set forth below to provide a sufficient understanding of embodiments of the invention. Embodiments of the invention may be practiced, however, without various of these particular details. In some instances, various aspects have not been shown in detail, in order to avoid unnecessarily obscuring the described embodiments of the invention.

Embodiments of the present invention may address individual drawbacks or combinations of drawbacks of other techniques described herein. However, the drawbacks and advantages described herein are provided by way of example only and are not intended to be limiting. All embodiments described herein may address all described limitations or have all described advantages. Some embodiments may not address any described limitations or have any of the described advantages.

Methods and systems are described for enriching nucleic acid samples. Example embodiments provide for rapidly and reproducibly enriching signal content in nucleic acid samples by reducing high abundance and repetitive nucleic acids. Example systems described herein provide an automated platform capable of carrying out microfluidic normalization-based and capture-based nucleic acid signal enrichment suitable for SGS. The platform is capable of performing denaturing and annealing of small nucleic acid samples, followed by a physical separation step in a microfluidic hydroxyapatite (or other affinity based) chromatography device. In at least some embodiments, the platform is flexible, allowing either enrichment mode to be used, alone or in tandem. Moreover, the platform is multiplexed in some embodiments, to enable multiple samples to be processed at a time (eight samples in one embodiment), to dramatically improve overall throughput. Although the initial focus is on SGS applications, the systems and methods described herein are broadly applicable to a wide range of non-sequencing applications that would benefit from reduction of high abundance or repetitive nucleic acids in a sample.

The various embodiments described herein provide microfluidic approaches for carrying out HAC normalization and capture-based signal suppression of nucleic acid samples for sequencing applications. In at least some embodiments, the systems are capable of performing two different modes of nucleic acid suppression—HAC-mediated normalization and nucleic acid capture—using the same hardware. Additionally, at least some of the embodiments of the system may be used to process a wide range of volumes and sample amounts. In some embodiments, the system is multiplexed to allow for processing of up to eight samples in a single cycle. In alternative embodiments, the system may be adapted to process less than eight samples or more than eight samples in a single cycle. Furthermore, some embodiments of the system are automated, to allow non-experts to operate the system hardware.

By providing for HAC mediated normalization and affinity binding and capture carried out in a microfluidic device, and by automating the HAC normalization process and the affinity binding and capture process, various embodiments described herein provide a number of advantages over prior art systems and methods. For example, embodiments described herein, as compared to prior art systems, generally use small volumes and small sample amounts, reduce sample-to-sample contamination, reduce non-specific losses, allow for flexibility of sample volumes and sizes (micro to mesoscale), enhance speed and reproducibility of the process, and/or reduce the amount of labor required to perform the process. Additionally, at least some embodiments of the systems described herein allow the HAC normalization process and the affinity binding and capture process to be conducted using the same system hardware. For example, both modes may be carried out on the same sample(s) sequentially, according to some embodiments.

An additional advantage, described more fully below, is the ability to multiplex samples—e.g., process as many as eight samples at a time in one embodiment (more than eight in alternative embodiments). Additionally, at least some embodiments of the systems described herein have relatively small footprints, allowing the systems to be co-located, and ultimately interfaced, with a library preparation device leading to a sequencer (e.g., MiSeq).

In general, in some embodiments, the HAC methods and systems described below use convenient, re-packable, microfluidic cartridges that are rapid, reproducible, and amenable to future automated sample preparation platforms. Small volume cartridges, for example as small as 2.5 μL, but not limited to, packed with commercially available HAC media, allow nucleic acid fractionation to be carried out in a matter of minutes, with sample sizes that are compatible with standard molecular biology protocols and kits.

The microfluidic HAC systems and methods described herein reduce or eliminate at least some of the drawbacks of prior art systems and methods and represent a viable alternative to DSN normalization. In tests, one embodiment of the HAC-based system described herein effectively and reproducibly separated ssDNA and dsDNA fractions from a complex nucleic acid population (human PBMC cDNA), enabling depletion of rRNA and concomitant enrichment of low-abundance RNA species to degrees comparable to those achieved through DSN-based normalization. The described HAC-based systems and methods feature several advantages, as mentioned above, including greater flexibility in hybridization conditions that would otherwise damage or inhibit DSN enzymatic function (addition of formamide and different hybridization temperatures, for example). Moreover, the described HAC methods are non-destructive, preserving the dsDNA fraction for further analysis, if desired. This may be especially useful in the case of highly complex environmental samples, the microbial composition of which is typically determined through comprehensive profiling of rRNA species.

As mentioned above, another alternative approach for nucleic acid signal enrichment/suppression is based on the selective capture of unwanted sequences. Commercially available kits enable capture-based enrichment of libraries for the human exome. However, these kits are not versatile; they have very limited utility outside of human SNP detection. A newer technology, developed by the assignee of the present application, involves customizable capture of nucleic acids using biotinylated probes. This customizable capture method can be used in a variety of research fields and can easily be customized to study any organism. Customizable capture works on the principle of using biotinylated nucleic acids as probes for binding and collection of complementary nucleic acids for sequencing ("enrichment") or removal from the library ("depletion"). Collection is mediated through interaction between the biotin moiety of the probe and an avidin matrix. This technique works for the study of genomic DNA (gDNA), as well as both single stranded and double stranded complementary DNA (cDNA), as long as each end of the nucleic acid bears a tag that supports selective amplification following capture. The customizable capture method may be used in a microfluidic-based system, such as the various embodiments described below. In various embodiments, this capture method may carried out in the same system hardware that is also used for HAC normalization.

As used herein, the term "sample" refers to any suitable sample that may be separated into two or more parts using any of the embodiments of the systems described herein. The examples below generally describe enrichment of nucleic acid samples, but these examples should in no way be interpreted as limiting the scope of the invention to a particular nucleic acid sample or type of sample.

Figure 2:
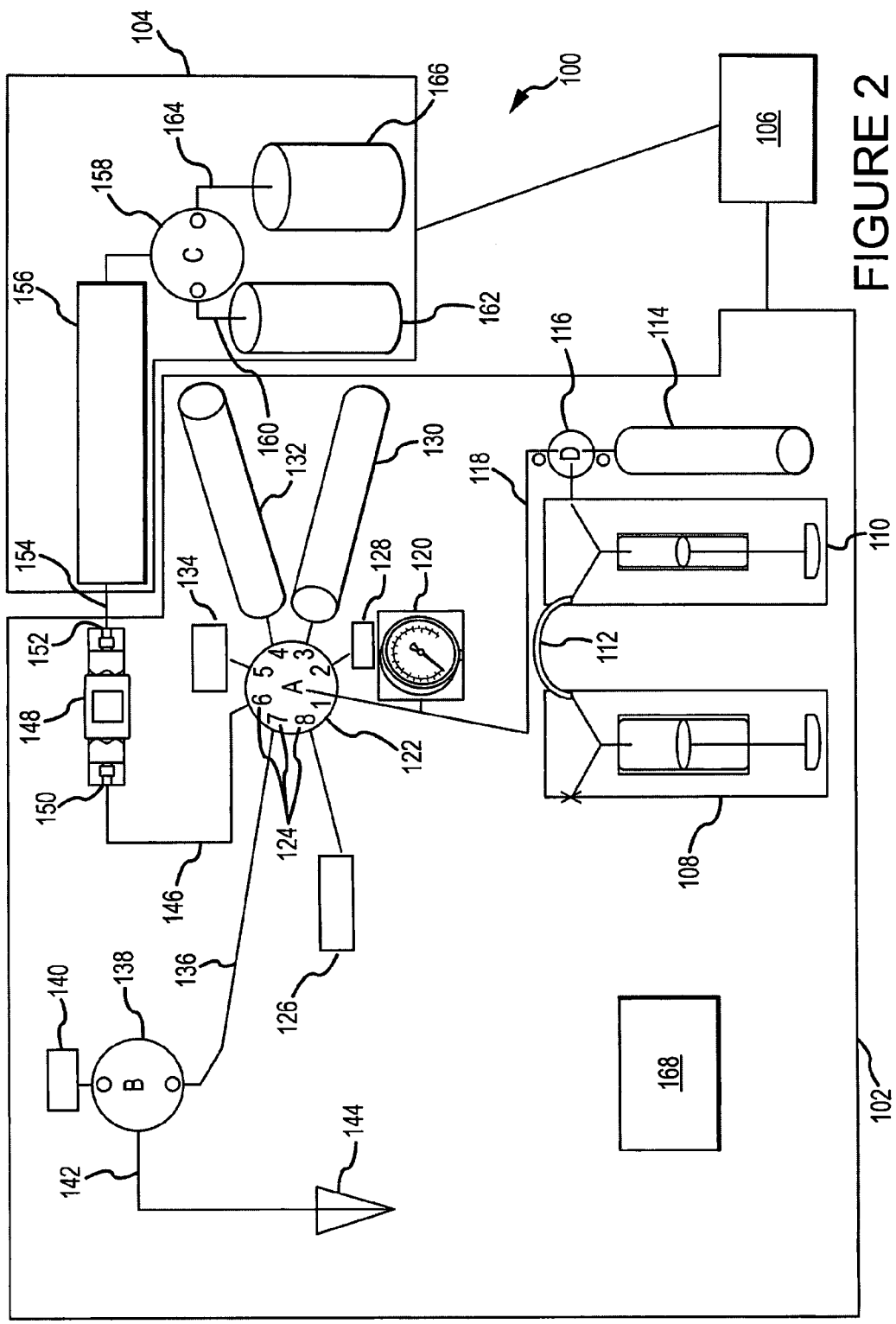
FIG. 2 is a diagram illustrating an automated, single-sample system for enriching nucleic acid samples, according to one embodiment.

Referring now to FIG. 2, one embodiment of a nucleic acid enrichment system 100 may include a first thermal enclosure 102, which houses a portion of the system 100, a second thermal enclosure 104, which houses another portion of the system 100, and a controller 106, which is coupled to one or more components of the system 100 and which is used to control operation of the system 100. In FIG. 2, the controller 106 is shown as connected to the thermal enclosures 102, 104, but this is merely pictured as such for simplicity of description. In actual embodiments of the system 100, the controller 106 may be attached electronically to one or more of the system components housed within the thermal enclosures 102, 104, rather than the enclosures themselves. In various embodiments, the controller 106 may be connected to system component(s) via wired connection, wireless connection, or a combination of both.

The embodiment of the system 100 for enriching nucleic acid samples diagrammed in FIG. 2 is an automated, HAC microfluidic system that is not multiplexed. Because it is not multiplexed, it is configured to process/enrich one nucleic acid sample at a time and is thus a simpler system than some of the multiplexed embodiments described below. In various alternative embodiments, the systems and methods described herein may be either automated but not multiplexed or automated and multiplexed.

In this embodiment, the portion of the system 100 enclosed in the first thermal enclosure 102 includes a buffer pump 108, a sample pump 110 connected to the buffer pump 108 via tubing 112, a wash buffer container 114 coupled with the sample pump 110, a valve D 116, tubing 118 that connects valve D 116 with a valve A 122, a pressure transducer 120, two elution buffer containers 130, 132, a valve B 138, tubing 136 connecting valve A 122 with valve B 138, a denaturing chamber 144, tubing 142 connecting valve B with the denaturing chamber 144, an HAC cartridge 148, tubing 146 connecting valve A with the HAC cartridge 148, and a temperature controller 168. The portion of the system 100 contained in the second thermal enclosure 104 includes a valve C 158, tubing 154 connecting the HAC cartridge 148 with the valve C 158, a conductivity detector 156 disposed along the tubing 154, a fraction collection container 162, a waste container 166, and tubing 160, 164 connecting valve C 158 with the fraction container 162 and the waste container 166. These components will be described in further detail below, along with other components not listed here.

In the embodiment shown, the portion of the system 100 housed in the clear plastic thermal enclosure 102 includes the temperature controller 168 (or "heating unit" or "heater"), to allow the system 100 to be operated at a wide range of close-loop controlled temperatures. Depending on the needs of the analysis (e.g., elevated temperature to minimize secondary structure formation in ssDNA), a user can select a desired enclosure temperature. In one embodiment, for example, the temperature controller may be a commercially available 250 watt forced air heater assembly from Hammond Manufacturing. This heater 168 uses resistance heating elements with a temperature limiter. In one embodiment, to improve control and reduce temperature fluctuations, the wiring of the stock cabinet heater assembly 168 may be modified, to separate the fan control from the heater control. A small control box (not shown) may be attached to the temperature controller 168 to provide the 115 VAC interconnects as well as the logic level power supply needed by the temperature controller 168 and display. In one embodiment, to maintain a desired cabinet temperature, the temperature controller may also include a separate microprocessor based temperature controller with a SSR output (for example, a Crydom MCTC2425KLA controller). The Crydom MCTC2425KLA controller uses a type K thermocouple to sense the temperature of the cabinet. A user controlled potentiometer on the front panel may be used to control the desired heater set point. This particular version of the Crydom MCTC2425KLA controller allows temperature control between 100 F and 400 F. To provide feedback to the operator, an independent digital thermometer may be used to monitor the temperature of the first thermal enclosure 102.

In one embodiment, the system may also include custom control software and a graphic user interface (not shown), which allow "scripts" to be written as needed to perform various steps in the process. A pressure transducer 120 may be connected to the system 100 to monitor operating pressures, and a conductivity detector 156 may be used to determine sample arrival and subsequent actuation of a valve to begin fraction collection.

In various embodiments of the system 100, microfluidic cartridges 148 (leak-proof 1 microliter to milliliter cartridges for bioanalysis) may be used, in sizes ranging from about 2 microliters to about 30 microliters. The cartridges 148 may be capped and sealed at each end with a nut threaded to connect to CapTite® fittings to facilitate fluid connections. A wide range of internal column volumes and dimensions (e.g. ratio of column diameter to length) may be used, for example in the range of about 1 microliter to about 30 microliters, all with a ratio of column length to diameter of approximately 10. The wide range of microfluidic cartridge volumes ensures that the system 100 is not limited to small volumes. Samples from the low microliter range all the way up to hundreds of microliters can be processed simply by selecting the microfluidic device volume and syringe pump barrel volume.

In one experimental embodiment, the column packing material was BioGel HTP DNA grade media, hydrated with 10 mM sodium phosphate pH 7.0, 0.005% (w/v) SDS (Buffer A) or similar buffer and de-fined according to manufacturer's guidelines prior to use. The microfluidic cartridges 148 were slurry packed under house vacuum, and the gel was retained in the column body with 35 μm pore size PEEK mesh. Two commercial PSD4 syringe pumps 108, 110 (Hamilton; Reno, Nev.) were used to control fluid flows through the system 100.

Two sizes were used: 2.5 mL and 125 μL. The smaller sample pump 110 was used to flush elution and wash buffers through the microfluidic cartridge 148, while the larger buffer pump 108 was useful for all other routing of fluids in the system. A custom 8-port multiport valve 122 was used for directing the fluid flow. The fluidic system used a multiport valve 122 and holding coil 118 approach, which allowed the fluids to be precisely routed to a variety of places in the system 100 with a minimum of pumps and other hardware.

For ease of description and understanding, the embodiment of the nucleic acid enrichment system 100 illustrated diagrammatically in FIG. 2 will now be described in terms of a DNA normalization method that may be carried out using the system 100. In general, any nucleic acid normalization process is composed of three main components: 1) denaturing a nucleic acid ("NA") sample into single stranded form; 2) partially rehybridizing (or "reannealing") the sample, producing a mixed population of single stranded and double stranded nucleic acids; and 3) separating single stranded and double stranded nucleic acids. Unlike currently available nucleic acid enrichment systems and methods, in the embodiments described in this application, the third, separation step is performed using hydroxyapatite chromatography in a microfluidic device.

In one embodiment, a method for using the system 100 may first involve initializing the stepper motor driven syringe pumps 108, 110, followed by rinsing and/or priming of various fluid lines of the system 100. The microfluidic device 148 may then be flushed, for example sequentially flushing with 20 column volumes each of 100 mM sodium phosphate pH 7.0, 0.005% (w/v) SDS (Buffer B), 320 mM sodium phosphate pH 7.0, 0.005% (w/v) SDS (Buffer C), and then Buffer A again.

After flushing the system 100, the normalization/nucleic acid enrichment method can be started by loading a sample into the denaturing chamber 144. The sample may be contained in a PCR (polymerase chain reaction) tube, for example, which may also be referred to herein as a "sample vial" or "sample container." The sample container may be loaded into the chamber 144, and the open end of the tubing 142 may be advanced into the sample container, as illustrated schematically in FIG. 2. The method may next involve denaturing the sample by raising the temperature in the chamber 144 to at least approximately 95 Celsius for several minutes. The sample is then partially rehybridized (or "reannealed") by lowering the temperature in the chamber 144 to an appropriate level for rehybridization and maintaining that temperature for a sufficient period of time to allow a desired mixture of ssDNA and dsDNA to form, typically about 1-5 hours. In some embodiments, the denaturing chamber 144 may be a heater referred to herein as a "cathedral heater," which will be described in greater detail below. One of the features of some embodiments of the cathedral heater is a heated lid that minimizes evaporative loss in the sample vial. During this time, the most abundant NA sequences find their complement strands the most rapidly and make up the majority of the double stranded NAs.

After a suitable period of time (dictated by the sample being processed and the specific normalization goals), the sample is diluted with buffer to essentially stop further hybridization. This step is performed by switching valve B 138 to inline (the dot adjacent the tubing 136) and valve A 122 to position 7. (Valve A 122, in this embodiment, is a multiposition valve, having eight positions 124.) The buffer pump 108 is then activated (e.g., the plunger depressed) to advance buffer through the tubing 118, valve A 122, tubing 136, valve B 138 and tubing 142, into the sample vial. In the embodiments herein, buffer will typically be phosphate buffer, and different types of buffer (for example, elution buffer and wash buffer) refer to different concentrations of phosphate buffer. In alternative embodiments, other buffers may be used.

In some embodiments, the buffer pump 108 and the sample pump 110 may be syringes or other syringe-like pumps, connected in series by tube 112 and having two different volumes (larger buffer pump 108 and smaller sample pump 110). The system 100 does not require two pumps, however, and alternative embodiments may include only one pump. Two pumps are included in the embodiments described herein, so that different volumes of buffer and sample can be moved through the system with a greater level of control than might be possible using just one pump. Two pumps of different volumes allow for flexibility in flow rates, which provides flexibility in the possible sample sizes that can be processed. In other alternative embodiments, more than two pumps may be used, if it would be desirable to have additional volume choices. Additionally, according to various alternative embodiments, any suitable type (or multiple types) of pump may be used. Any suitable mechanism for pumping fluid through the system 100 may be used, in various embodiments, such as but not limited to positive displacement pumps, velocity pumps, impulse pumps, gravity pumps and valveless pumps. Although syringe pumps 108, 110 are shown in the various figures herein, these pumps are shown for exemplary purposes only and should not be interpreted to limit the system 100 to any particular type or size of pump.

The next step in the nucleic acid normalization process involves applying the diluted sample to the hydroxyapatite chromatography (HAC) microfluidic device 148. Although FIG. 2 illustrates the example of a microfluidic HAC cartridge, this is simply one example of a HAC microfluidic device 148 and is not intended to limit the scope of the disclosed embodiments. Instead, any suitable configuration of HAC microfluidic device 148 may be included in the system 100, according to various embodiments. With valve A 122 still in position 7, the sample pump 110 may be activated (e.g., pulled back) to draw the sample fully into the tubing 118 between valve A 122 and the pumps 108, 110—a large volume length of tubing, also called the "holding coil." Valve A 122 may then be switched to position 6, and the sample pump 110 may again be used (e.g., the plunger depressed) to advance the sample out of the holding coil 118, through tubing 146 and into the HAC microfluidic device 148. The microfluidic device 148 includes an inlet 150 and an outlet 152.

In this embodiment, the process next includes filling the sample pump 110 with fresh buffer from the wash buffer container 114. This is accomplished by first switching valve D 116 to open toward the wash buffer container 114 and drawing back the plunger of the sample pump 110 to draw fresh buffer into the sample pump 110. Next, the direction of valve D 116 is switched to face toward tubing 118, and the plunger of the sample pump 110 is depressed to dispense buffer through the HAC microfluidic device 148 to drive the sample through the HAC microfluidic device 148 and to flush out any non-specifically bound sample.

The next step in the process is to elute the single stranded NAs from the sample. This is achieved by switching valve A 122 to position 3 and drawing elution buffer from the first elution buffer container 130 into the holding coil 118 using the sample pump 110. Valve A 122 is then switched to position 6, and the single strand elution buffer is flushed through the HAC microfluidic device 148 by depressing the plunger of the sample pump 110. The conductivity detector 156 monitors the output from the outlet 152 of the HAC microfluidic device 148 and indicates when the elution buffer has reached the outlet 152. At that time, the system 100 switches valve C 158 from waste 166 to a waiting vial 162 for collection. The sample passes through the tubing 154, past the conductivity detector 156, through valve C 158, through tubing 160, and into the sample collection container 162. Double strand elution can then proceed, if desired, by following the same procedure as the single strand elution except the elution buffer will be drawn from the second elution buffer container 132 (position 4 on valve A instead of position 3). In some embodiments, double stranded NA may be directed into the waste container 166, while in alternative embodiments, the double stranded NA may be directed into a second sample collection container 162. In one embodiment, the sample is flushed through the microfluidic device 148 with Buffer A, ssDNA is eluted using Buffer B, and dsDNA is eluted using Buffer C.

The conductivity detector 156 (in one embodiment a contactless conductivity sensor (eDAQ)) may be used as an indicator of sample arrival. The fraction collection valve C 158 may be controlled, using information regarding sample arrival from the conductivity detector 156, to switch the fluid output between waste 166 and fraction collection 162 positions.

In the embodiment shown, valve A 122 may include additional positions 124, not described above. For example, position 8 may open to an additional sample container 126, position 5 may open to a waste container 134, and position 2 may open to a vent 128. In various alternative embodiments, valve A 122 may have additional or fewer positions. Valve B 138, valve C 158 and valve D 116 are each 2-position, 3-port valves. In other words, each of those three valves 138, 158, 116 is moveable between two positions and has three ports. Valve B 138, for example, has a port facing the tubing 136, another port facing the tubing 142, and a third port that is a vent 140. Valve C 158 has a port facing the tubing 154, a port facing tubing 160, and a third port facing tubing 164. Valve D 116 has a port facing the wash buffer container 114, a port facing the sample pump 110, and a port facing the tubing 118. In various alternative embodiments, additional valves may be included for various purposes and at various locations in the system 100, as needed.

In the embodiment shown, the system 100 also includes a pressure transducer 120, coupled with the tubing 118. The pressure transducer 120 measures pressure in the tubing 118, so that a user may monitor pressures in the system 100 and prevent over-pressurizing the system 100. In alternative embodiments, the pressure transducer 120 may be attached to some other part of the system 100. Typically, the pressure transducer 120 will be located somewhere in the system 100 so that it is in fluid communication with the pumps 108, 110 (or single pump in alternative embodiments).

The majority of the method described above is typically carried out in the first thermal enclosure 102 at an elevated temperature of approximately 50 degrees Celsius. The elevated temperature is maintained by the temperature control unit 168 (or "heater") inside the first thermal enclosure 102. The controlled temperature helps ensure that secondary structure in the single stranded NAs (folding on themselves to form double stranded sections) is minimized and the single stranded NAs properly elute in the appropriate fraction. As illustrated in FIG. 2, the tubing 154 extends from the first thermal enclosure 102 into the second thermal enclosure 104. The second thermal enclosure 104 is separate from the first enclosure 102, because the temperature of the second enclosure 104 is typically held at a lower, chilled temperature, to help preserve the samples. Both enclosures 102, 104, when taken together, may have a relatively small total footprint, such that the entire system 100 may fit on a wheeled cart or small table for easy portability.

The controller 106 may include a specialized electronic control unit (or "box"), a laptop or desktop computer, multiple electronic control units, or any combination thereof. The controller 106 may be coupled with any combination of components of the system 100, such as but not limited to the temperature control unit 168, the pumps 108, 110, the conductivity detector 156, the valves A 122, B 138, C 158 and D 116, and the sample collection container 162. The controller 106 generally allows for at least part of the method described above to be automated. For example, in one embodiment, a user may manually load a sample into the denaturing chamber 144, and all other steps of the described method may be performed automatically, controlled at least in part by the controller 106.

Multiplexing

In various alternative embodiments, the single sample system 100, described above, may be adapted to allow multiple samples to be processed in parallel by an automated system, thereby dramatically increasing the utility of the platform. These multiple-sample systems, several embodiments of which are described below, are referred to herein as "multiplexed" systems.

Figure 3:
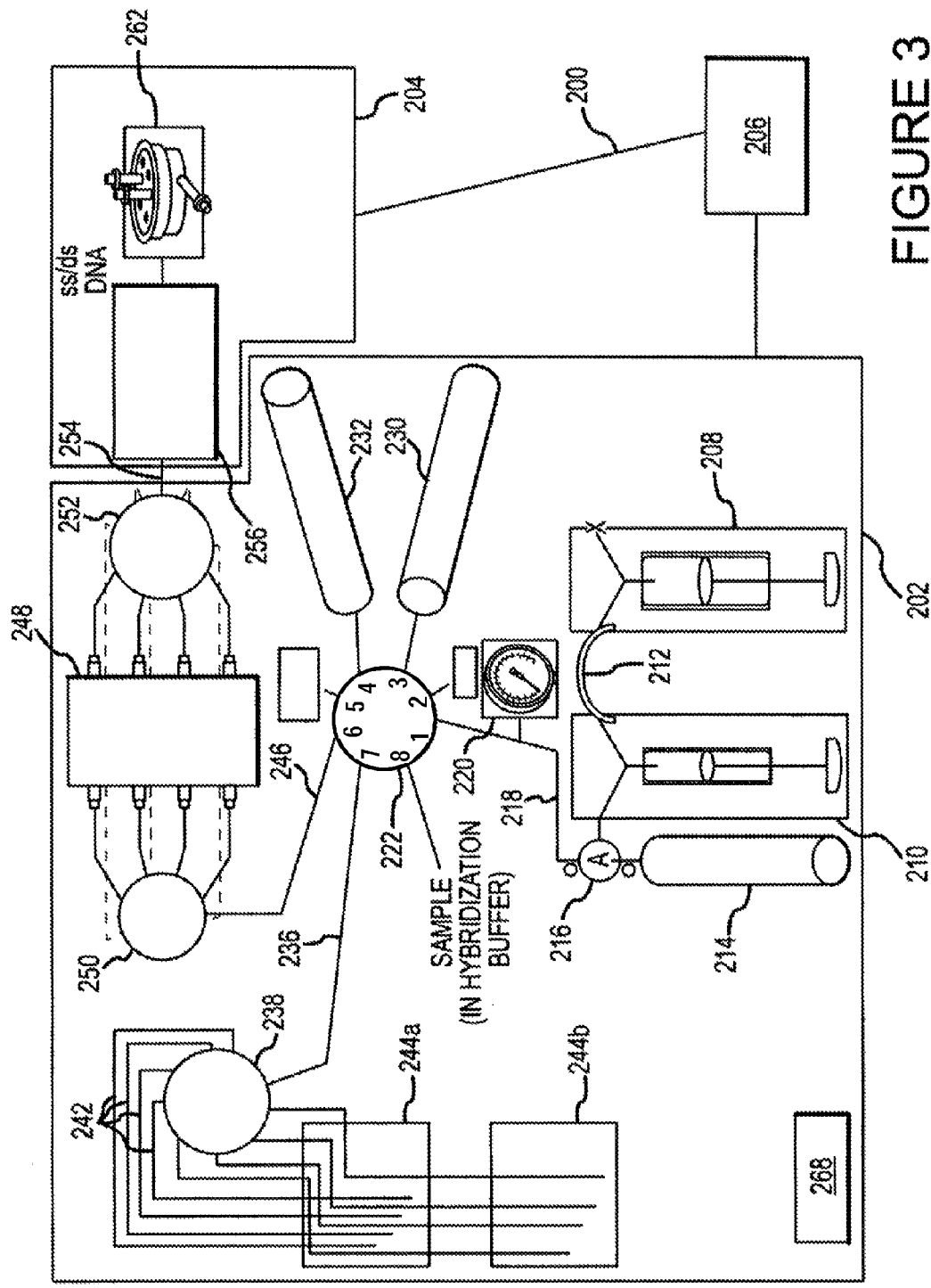
FIG. 3 is a diagram illustrating an automated, multiplexed system for enriching nucleic acid samples, according to one embodiment.

Referring now to FIG. 3, in an alternative embodiment, a system for enhancing nucleic acid samples 200 may be automated and multiplexed. Multiplexing allows multiple samples (typically but not necessarily nucleic acid samples) to be processed at the same time within the system 200. Again, different portions of the system 200 may be enclosed a first thermal enclosure 202 and a second thermal enclosure 204, and the system includes a controller 206, which is coupled with various components of the system 200 (illustrated schematically by two connecting lines in FIG. 3). Many components of the system 200 of FIG. 3 are the same or analogous to components described in reference to the embodiment in FIG. 2, and those components will not be described again in detail.

In this embodiment, the portion of the system 200 enclosed in the first thermal enclosure 202 includes a buffer pump 208, a sample pump 210 connected to the buffer pump 208 via tubing 212, a wash buffer container 214 coupled with the sample pump 210, a system valve 216, tubing 218 that connects the system valve 216 with a distribution valve 222, a pressure transducer 220, two elution buffer containers 230, 232, a sample valve 238, tubing 236 connecting the distribution valve 222 with the sample valve 238, two cathedral heater denaturing chambers 244*a* and 244*b*, and tubing 242 connecting the sample valve with the denaturing chambers 244*a* and 244*b*. The first thermal enclosure 202 also encloses a multiplexed, microfluidic HAC "bus" 248, an inlet valve 250 for the bus 248, an outlet valve 252 for the bus, tubing 246 connecting the distribution valve 222 with the inlet valve 250, a portion of the tubing 254 connecting the outlet valve 252 with a sample fraction collector 262, and a temperature controller 268. The portion of the system 200 contained in the second thermal enclosure 204 includes a portion of the tubing 254, a conductivity detector 256 and the sample fraction collector 262.

The multiplexed system 200 and its associated method of use are analogous to the system and method described in reference to FIG. 2 but include a number of different and additional features to allow for multiplexed nucleic acid sample processing. In this embodiment, the system 200 allows for the processing of eight samples at the same time. The two cathedral heaters/denaturing chambers 244*a* and 244b each allow for denaturing and rehybridizing of four samples at once. Tubing 242 connects each of eight sample reservoirs in the cathedral heaters 242 with the sample valve 238. Each sample may then be passed individually through tubing 236 and 246 and the distribution valve 222 and inlet valve 250 into the microfluidic bus 248. The microfluidic bus 248 includes eight HAC microfluidic columns for further processing/eluting the NA samples individually, after which the samples pass through the outlet valve 252 and onto the fraction/sample collection reservoir 262. In one embodiment, the fraction collection reservoir may include 32 reservoir positions, for collecting two samples and two waste deposits from each of the eight columns of the microfluidic bus 248. The term "column" is used herein to refer to a portion of a microfluidic device through which a sample is processed, typically though not necessarily a HAC column portion of a microfluidic device. "Column" should not be interpreted herein as being limited only to one capillary of a microfluidic device.

The method for using this embodiment of the system 200 is largely the same as that described above, except for the significant and advantageous difference that eight samples can be processed at once. The overall process may begin by denaturing four samples simultaneously in the first cathedral heater 244a, after which the temperature is dropped to the annealing temperature and maintained for the requisite amount of time (e.g., approximately 5 hours). After a time delay (e.g., approximately 1 hour) the second cathedral heater 244b is used to denatured and anneal the second set of four samples. Once the first annealing time period is completed, the four samples are diluted (e.g., 1 to 5) with buffer A, to essentially stop further annealing, and the samples are sequentially flushed through individual HAC columns of the microfluidic bus 248 and the ssDNA and dsDNA fractions are collected in the fraction collector 262. By the time the last of the first four samples has been flushed through the columns and eluted, the second cathedral heater 244b will be ready to be diluted prior to performing HAC. The staggered start times allow for the chromatography to be completed on the first four samples by the time the second ones are ready. The dilution of the four samples in each cathedral 244a, 244b prior to HAC ensures that the four samples experience essentially the same amount of annealing time, since the dilution step effectively drops the rate of annealing 25 fold. The few minutes time difference at 25-fold reduced rate will be insignificant compared to the total annealing time. This overall approach enables the denaturing and annealing of up to eight samples without requiring eight separate heaters.

In this embodiment, the sample valve 238, inlet valve 250 and outlet valve 252 are all multi-port, multi-position valves configured to selectively address each sample and apply it to its own individual microfluidic column (or "tube"), with at least nine ports on each valve 238, 250, 252, to accommodate one tube for each sample and one system tube leading into or out of the valve. The microfluidic bus 248 replaces the HAC cartridge of the previously described embodiment, and includes eight microfluidic columns in this embodiment. (Alternative embodiments may include fewer or more microfluidic columns.) The inlet valve 250 and outlet valve 252 are included in this embodiment, to specifically direct each sample into one of the microfluidic columns in the bus 248. The fraction collector 262 (or "sample collector") is configured to manage the larger number of collected fractions. For example, in one embodiment, the fraction collector 262 may be a 32-reservoir, rotating carousel, configured to collect two fractions and two waste fractions from each of the eight samples. One embodiment of the cathedral heaters 224a, 244b, the microfluidic bus 248 and the fraction collector 262 are described in more detail below.

The method may be performed such that each of the eight samples is moved through the system 200 in the same way as described above for the single-sample system. However, the eight samples may be moved serially through the system 200 into the microfluidic bus 248 and then passed individually and serially from the bus 248 through the rest of the system 200 to the fraction collector 262. In some portions of the system 200, each sample has its own, dedicated tubing (tubing 242, for example). In other portions of the system 200, the samples share a common tube and thus must travel through the tube sequentially (tubing 236, 218, 246 and 254, for example). As described previously, some or all of the nucleic acid enrichment method may be conducted automatically, controlled at least in part by the system controller 206. The combined automation and multiplexing of the nucleic acid enrichment process may greatly reduce the labor and time required to process NAs and may also make results more reproducible. For example, once the system 200 is set up, with samples located in the cathedral heaters 244a, 244b, it may be possible to perform the processing method with little or no human intervention, thus greatly reducing the labor required, compared with currently available methods.

Figure 4:
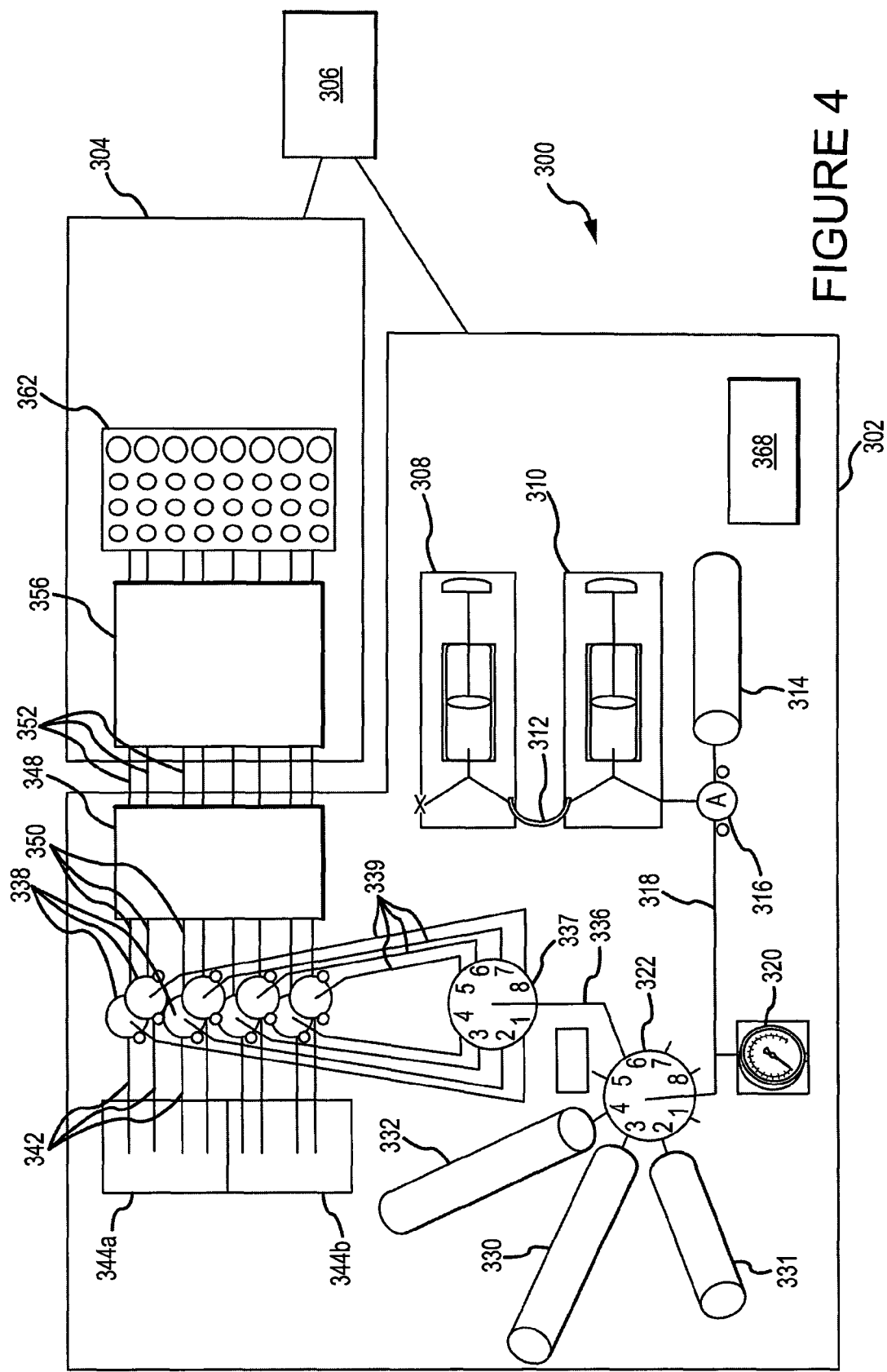
FIG. 4 is a diagram illustrating an automated, multiplexed system for enriching nucleic acid samples, according to an alternative embodiment.

Referring now to FIG. 4, in another alternative embodiment, an automated, multiplexed nucleic acid processing system 300 includes a controller 306 and may have a number of the features described for the previous system 200, with several additional features configured to keep the samples in separate, dedicated tubing throughout the procedure. In this embodiment, the portion of the system 300 enclosed in the first thermal enclosure 302 includes a buffer pump 308, a sample pump 310 connected to the buffer pump 308 via tubing 312, a wash buffer container 314 coupled with the sample pump 310, a system valve 316, tubing 318 that connects the system valve 316 with a first distribution valve 322, a pressure transducer 320, two elution buffer containers 330, 332, and a wash solution container 331. One added feature of this embodiment of the system 300 is a second distribution valve 337, coupled with the first distribution valve 322 via tubing 336. The second distribution valve 337 is coupled with eight sample valves 338 via eight tubes 339. Each sample valve 338 is configured to direct sample from one of two cathedral heaters 344a, 344b, through eight separate tubes 342, into eight additional separate tubes 350 and thus into the microfluidic HAC bus 348. After processing through the bus 348, each sample passes through another separate, dedicated tube 352, past an 8-head conductivity detector 356, into a fraction collector 362. Again, the fraction collector may, in some embodiments, have thirty-two reservoirs—four per sample. As with previously described embodiments, the first thermal container 302 may also contain a temperature controller 368 (or "heater").

The portion of the system 300 contained in the second thermal enclosure 304 includes a portion of the tubing 352, the conductivity detector 356 and the sample fraction collector 362. As mentioned above, the second thermal enclosure 304 will generally be kept at a lower temperature than that of the first thermal enclosure 302, in order to help preserve the collected fractions.

The method of using this embodiment of the system 300 will typically be very similar to that described previously, except that the system is multiplexed for processing of up to eight samples at once. In this system 300, each sample will be held separately, in separating tubing, during more of the process than in previously described embodiments. This separation of samples will likely help prevent sample contamination. Additional features of the system 300 in this embodiment, as compared to the multiplexed embodiment of the system 200 described above, include the second distribution valve 337, multiple tubes 339, 350, multiple sample valves 338, and the 8-headed conductivity detector 356. The conductivity detector 356 is configured to be in fluid communication with each of the eight tubes 352, so that it can detect conductivity of each sample after it exits the microfluidic bus 348.

Figure 5:
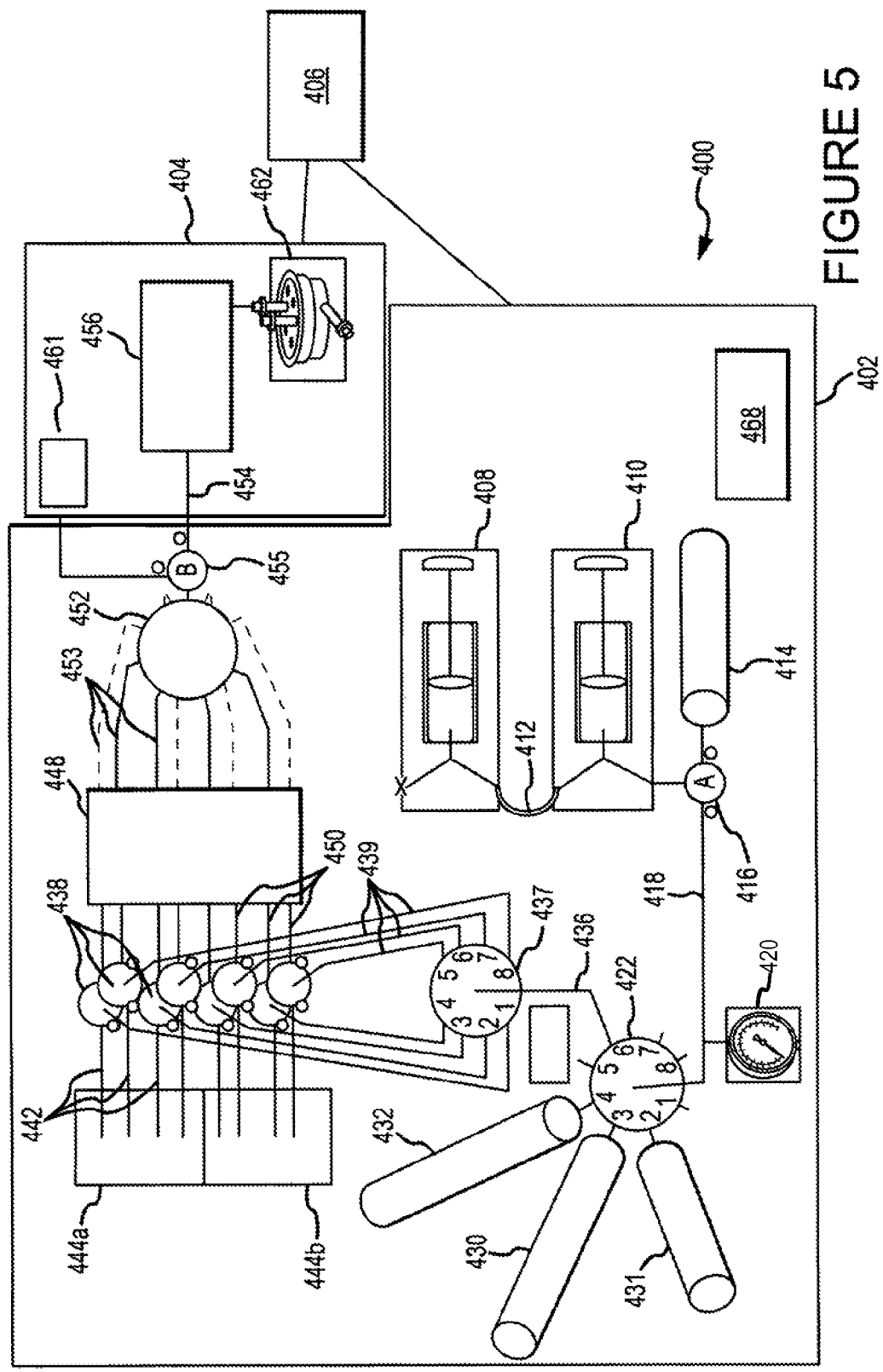
FIG. 5 is a diagram illustrating an automated, multiplexed system for enriching nucleic acid samples, according to another alternative embodiment.

Referring now to FIG. 5, in another alternative embodiment, an automated, multiplexed nucleic acid processing system 400 includes a controller 406 and may have a combination of some of the features of the previously described systems 200 and 300. In this embodiment, the portion of the system 400 enclosed in the first thermal enclosure 402 includes a buffer pump 408, a sample pump 410 connected to the buffer pump 408 via tubing 412, a wash buffer container 414 coupled with the sample pump 410, a system valve 416, tubing 418 that connects the system valve 416 with a first distribution valve 422, a pressure transducer 420, two elution buffer containers 430, 432, and a wash solution container 431. The system 400 also includes a second distribution valve 437, coupled with the first distribution valve 422 via tubing 436 and also coupled with eight sample valves 438 via eight tubes 439. Each sample valve 438 is configured to direct sample from one of two cathedral heaters 444a, 444b, through eight separate tubes 442, into eight additional separate tubes 450 and thus into the microfluidic HAC bus 448. After processing through the microfluidic bus 448, each sample passes through another separate, dedicated tube 453 and then through an outlet valve 452 and a collection valve 455. The collection valve 455 is used to separate samples, which continue into a tube and passes into a waste container 461. The tube 454 travels past a conductivity detector 456 to a fraction collector 462. As with previously described embodiments, the first thermal container 402 may also contain a temperature controller 468 (or "heater").

The portion of the system 400 contained in the second thermal enclosure 404 includes a portion of the tubing 454, the conductivity detector 456 and the sample fraction collector 462. It may also include the waste container 461, in some embodiments. As mentioned above, the second thermal enclosure 404 will generally be kept at a lower temperature than that of the first thermal enclosure 402, in order to help preserve the collected fractions.

Again, the method of using this embodiment of the system 400 is a multiplexed method. Much of the separate tubing described with reference to system 300 is included. However, one common tube 454 is used after processing in the HAC microfluidic bus 448. This common tube allows a 1-head conductivity detector to be used, rather than the 8-head conductivity detector described with reference to system 300. This allows for at least a simpler conductivity detector.

Figure 6:
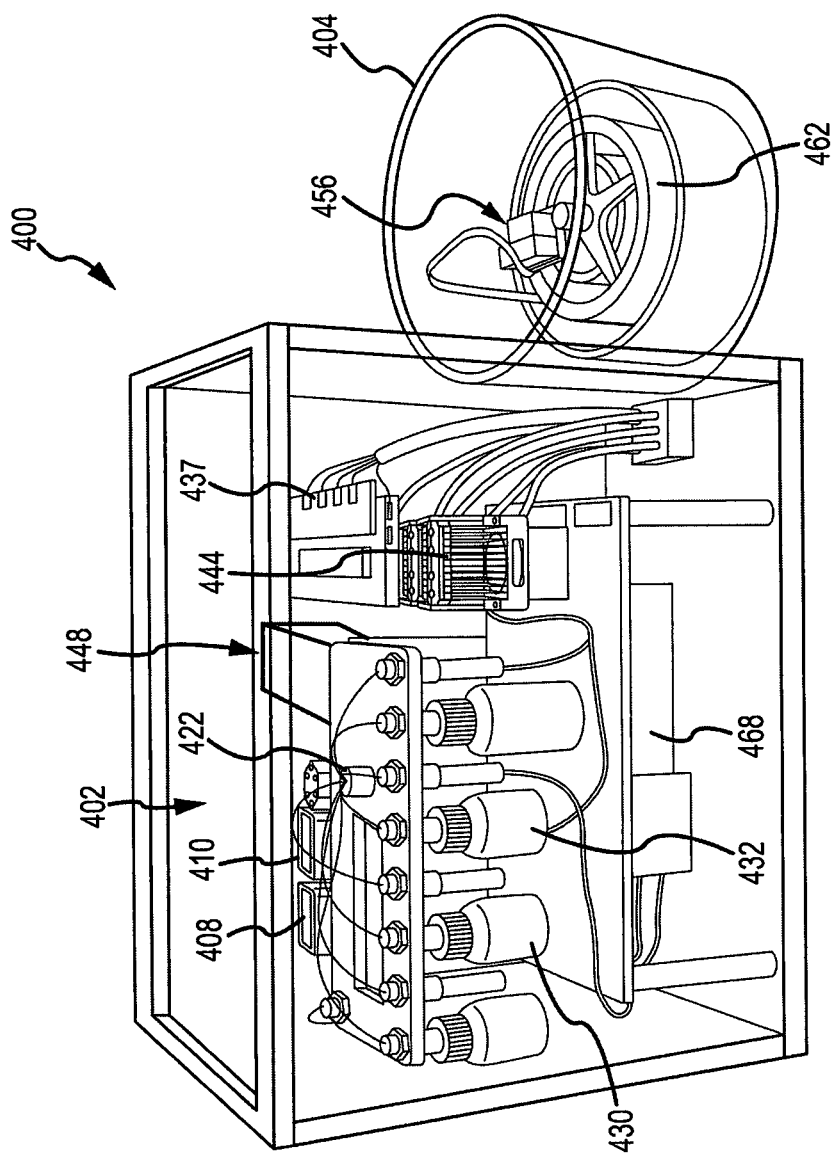
FIG. 6 is perspective view of the system of FIG. 5.

FIG. 6 is a perspective view of the system 400 of FIG. 5, illustrating some of the features of the system 400. The first thermal enclosure 402 houses the microfluidic bus 448, the distribution valves 422, 437, the pumps 408, 410, buffer containers 430, 432 and the temperature controller 468. The second thermal enclosure 404 houses the fraction collector 462 and conductivity detector 456.

Figure 7A:
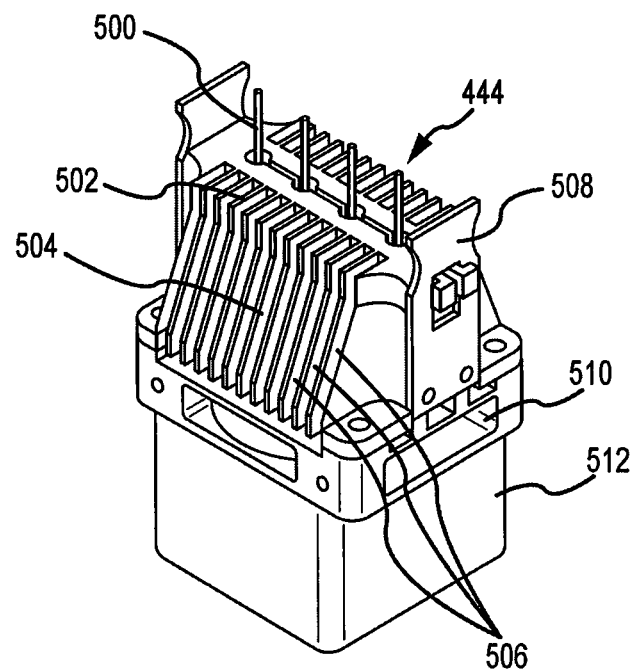
FIGS. 7a and 7b are perspective and side, cross-sectional views, respectively, of a cathedral heater for denaturing and re-annealing nucleic acids, according to one embodiment.
Figure 7B:
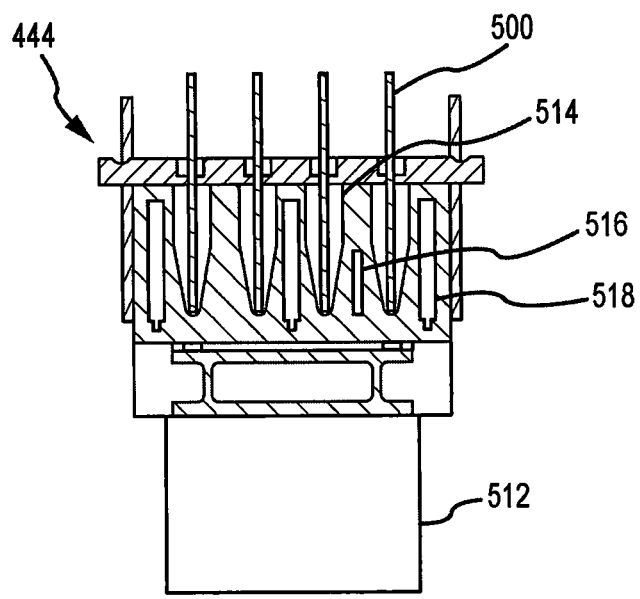

Referring now to FIGS. 7A and 7B, one embodiment of the cathedral heater 444 will be described in further detail. As mentioned previously, in one embodiment, the cathedral heater 444 is configured to hold four starting samples of nucleic acid and to denature and rehybridize those samples by increasing and then reducing their temperature. The cathedral heaters 444 are referred to as such due to their shape in the embodiment illustrated. They may also be referred to as "annealing chambers," "denaturing chambers," "heaters" or any other suitable terminology. In alternative embodiments, the cathedral heaters 444 may have a different overall configuration. As described above, in some embodiments, a nucleic acid denaturing system may include two cathedral heaters 444, which work in tandem to allow simultaneous processing of eight samples. In alternative embodiments, heaters may be configured to denature and reanneal fewer than four samples or more than four samples, and systems may include any number of heaters.

In one embodiment, the cathedral heater 444 is made primarily of a machined aluminum block 504 positioned on top of a cooling fan 512. For example, in one embodiment, the aluminum block is a 6061-T6 aluminum block. The block 504 may be machined to include multiple, integral cooling fins 506 to decrease the cooling time when an integral heater is shut off and the attached cooling fan 512 is energized. The block 504 may also include an integrated thermal cover 502 (or "heated lid"), microfluidic tubing 500, a thermal isolation spacer 510, and four reservoirs 514 (FIG. 7B). Elastic straps 508 may be used to attach the thermal cover 502 to the base of the reservoir block 504, and the cooling fan 512 may be attached to the bottom of the block 504. As illustrated in FIG. 7B, the cathedral heater 444 may also include a thermal sensor 516 and three cartridge heaters 518, implanted within the block 504. Each of the microfluidic tubes 500 is configured to allow placement of a PCR tube within it, such that one end of the PCR tube will reside within one of the reservoirs 514. The samples are placed in the reservoirs 514. After denaturing and reannealing, the samples are drawn out of the reservoirs 514, via the tubing 500, to enter the rest of the system for HAC microfluidic processing.

In one embodiment, the profile geometry of the cathedral heater 444 may be configured to optimize thermal contact with the reservoirs 514 and samples (in PCR tubes) placed in those reservoirs. For example, the block of aluminum 504 may be machined to accommodate a 0.125 inch diameter× 0.750 long block (or "cartridge") heater 518 (for example, Sunelectric, #H075-30-24-01), to provide heating, and a resistive thermal device 516 (for example, Minco, #S13282PE3T36) to monitor temperature. A programmable temperature control unit (for example, Omega CNI3243) may be used to complete the close-loop thermal control. Additionally, the aluminum block 504 may be machined to include cooling fins 506 and may be positioned over a small high flow fan 512 to assist in rapid cooling from the denaturing temperature to the annealing temperature. The thermal cover 502 is a separate piece relative to the block 504 and may be attached to the block via the elastic straps 508 (or via other attachment means in alternative embodiments). The thermal cover 502 may be heated separately from the block 504, in order to heat the lids of the sample vials at a slightly higher set temperature than the rest of the cathedral heater/annealing chamber 444 to reduce sample evaporation. To remove the reservoirs 514 from the block 504, the thermal cover 502 is simply removed, so that the reservoirs 514 may be taken out and replaced.

Figure 8A:
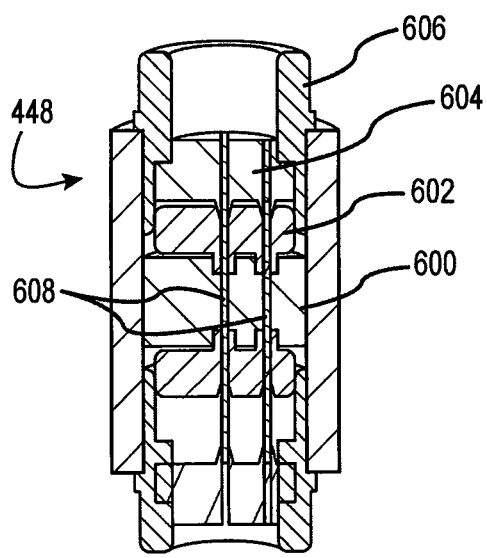
FIGS. 8A-8C are side partial cross-section, perspective and magnified views, respectively, of an 8-channel HAC microfluidic bus, according to one embodiment.
Figure 8B:
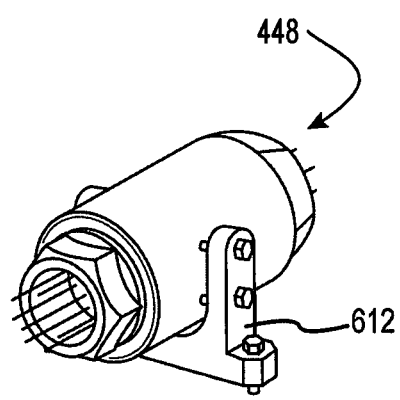
Figure 8C:
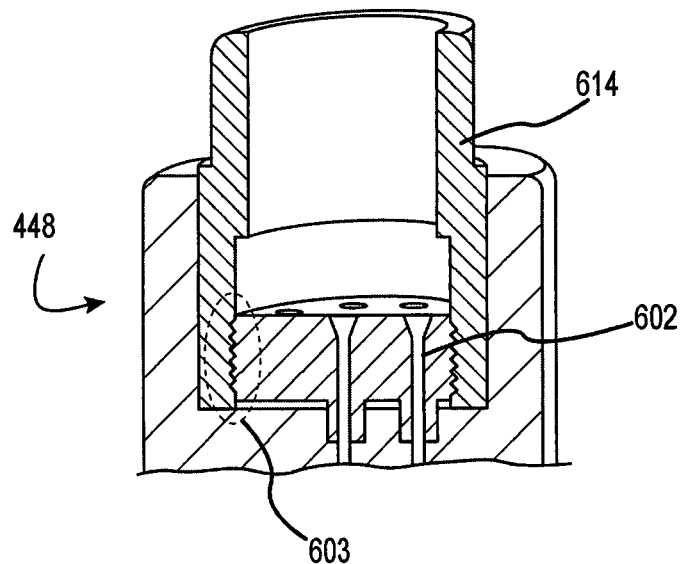

Referring now to FIGS. 8A-8C, in some embodiments, a nucleic acid processing system may include a HAC microfluidic bus 448, as mentioned above. In the embodiment shown, the microfluidic bus 448 is configured for processing eight samples. In alternative embodiments, the bus 448 may be configured to process any other number of samples, fewer than or greater than eight. The microfluidic bus 448 may include a cartridge body 600, a filter plug plate 602, a ferrule plate 604, a locking nut 606, and eight HAC columns 608 (or "capture columns"). The filter plug plate 602, the ferrule plate 604, and the locking nut 606 work together to form a seal around each of the columns 608. As illustrated in FIG. 8B, in some embodiments, the microfluidic bus 448 may be attached to another component of a nucleic acid enrichment system 400 via an attachment bracket 612. As illustrated in FIG. 8C, in one embodiment, an extraction nut 614 may be used to remove the filter plug plate 602, which has a threaded region 603, from the microfluidic bus 448, thus allowing the columns 608 to be repacked.

The microfluidic bus 448 may allow a variety of internal column volumes to be accommodated, based on predetermined diameter through-holes machined in the cartridge body 600. With the use of a custom, in-house developed adaptor, all eight columns can be packed simultaneously under vacuum, and the entire microfluidic bus 448 can be sealed to ⅟₃₂ inch tubes. The design allows for all eight connections to swage to the inlet and outlet tubing simultaneously when the ferrule plate 604 is tightened using the locking nut 606.

The columns 608 perform much the same as the individual column counterparts but are individually addressed via an eight port multivalve (or alternatively, eight separate tubes) leading into and out of the HAC microfluidic bus 448. Through the scripting, it is possible to selectively flush each column 608, and it is possible to send each sample to a different column 608. All columns 608 can be flushed during the annealing time in preparation for receiving samples. As with the single column design, the columns 608 are typically flushed prior to use. Columns 608 can be reused for future samples after flushing or can be repacked.

Figure 9:
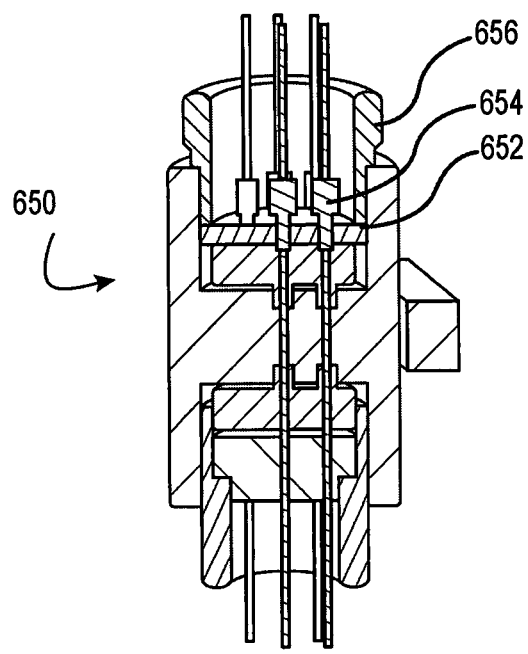
FIG. 9 is a side partial cross-section view of an 8-channel HAC microfluidic bus, according to an alternative embodiment.

With reference to FIG. 9, in an alternative embodiment, a HAC microfluidic bus 650 may include an optional individual ferrule attachment, including a locking nut 656, a standard ferrule 654 and a threaded plate 652. In this embodiment, the locking nut 656, the standard ferrule 654 and the threaded plate 652 work together to form the seal around the columns 608.

Figure 10:
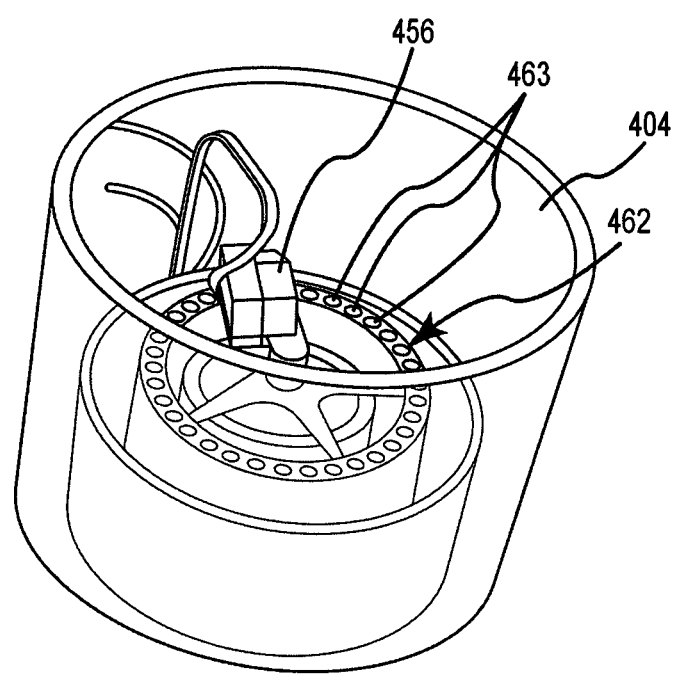
FIG. 10 is a perspective view of a fraction collector and conductivity detector, housed in a thermal enclosure, as part of a nucleic acid processing system, according to one embodiment.

Referring now to FIG. 10, in one embodiment, the second thermal enclosure 404 of the nucleic acid processing system 400 may house the fraction collector 462 (or "sample collector") and the conductivity detector 456. The second thermal enclosure 404 is configured to allow samples to be collected and maintained in the fraction collector 462 in a chilled environment, to help preserve the collected fractions. In one embodiment, the fraction collector 462 may be a cylindrical carousel with multiple containers 463 for containing fractions and optionally waste. In one embodiment, for example, the fraction collector 462 may place a waste vial between each fraction container 463. In some embodiments, no valves need to be actuated for fraction and waste collection. Instead, a stepper motor simply moves to the next position. This design minimizes contamination between collected fractions, since the same sample line is effectively cleared each with each sample. The second thermal enclosure 404 and cooled interior help preserve sample, limit evaporation, and prevent dust or other contamination from fouling the collection vials.

Experimental Data

Figure 11A:
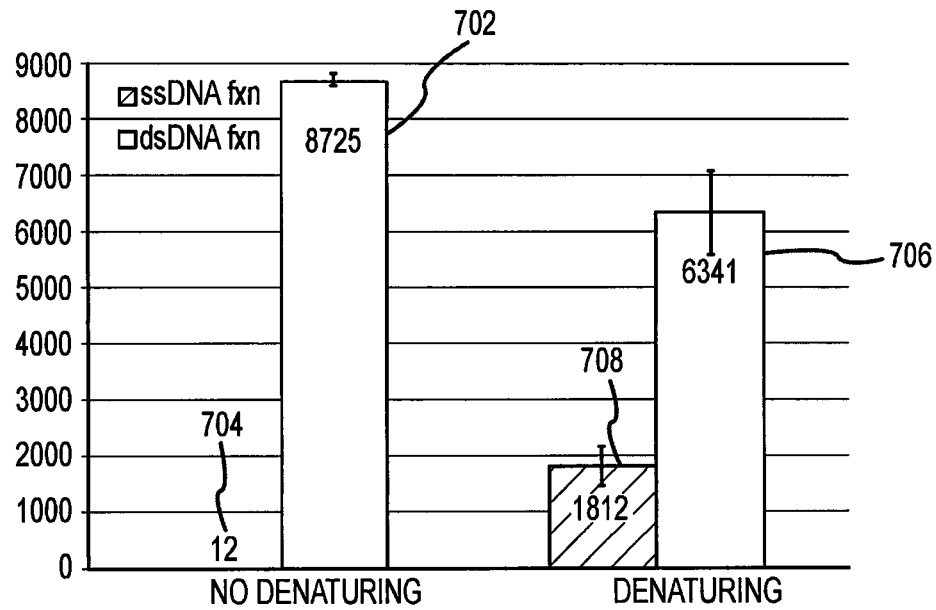
FIGS. 11A and 11B are bar graphs illustrating performance of a nucleic acid enrichment system, according to one embodiment.
Figure 11B:
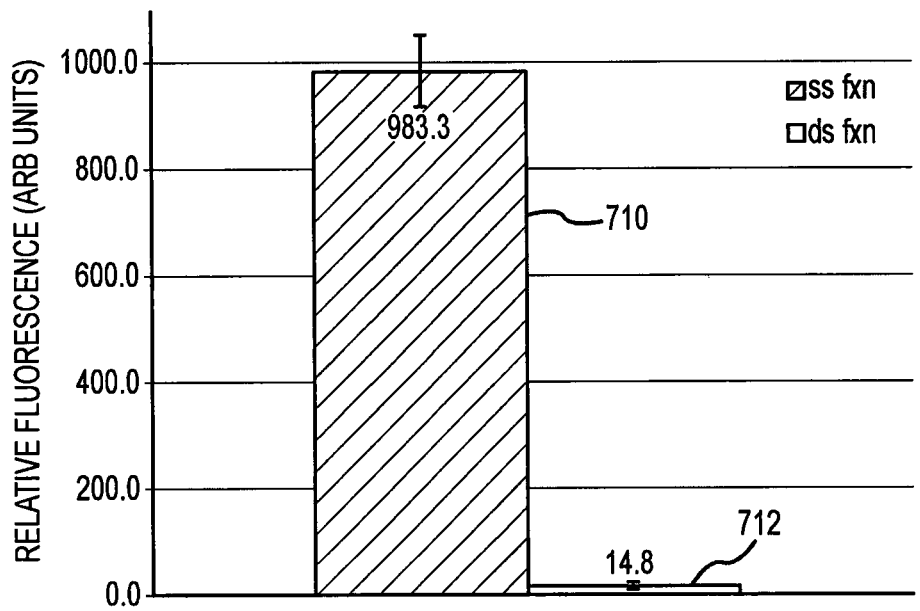

Referring now to FIGS. 11A and 11B, the overall performance of the automated, single-sample system 100 was demonstrated in the HAC normalization mode with a dsDNA 100 by size ladder (Invitrogen). Replicate samples first went through an annealing step without any denaturing followed by HAC separation in the automated system 100. As illustrated in FIG. 11A, without the denaturing step, almost all the sample remained dsDNA fraction 702, with almost no ssDNA fraction 704. In other words, the DNA was exclusively found in the dsDNA fraction 702, as expected for a fully dsDNA containing sample. Next, replicate samples in the annealing chamber were exposed to a denaturing step, followed by a brief annealing step and sent to the HAC microfluidic device for separation of ssDNA and dsDNA. Some of the DNA was single stranded 708, and some was double stranded 706, prior to hydroxyapatite chromatography. This is illustrated in the right hand portion of FIG. 11A. FIG. 11B illustrates reproducibility of replicate (N=5) samples of ssDNA, with a single stranded fraction 710 and essentially no double stranded fraction 712. The units in both FIGS. 11A and 11B are arbitrary, relative fluorescence units.

Figure 12:
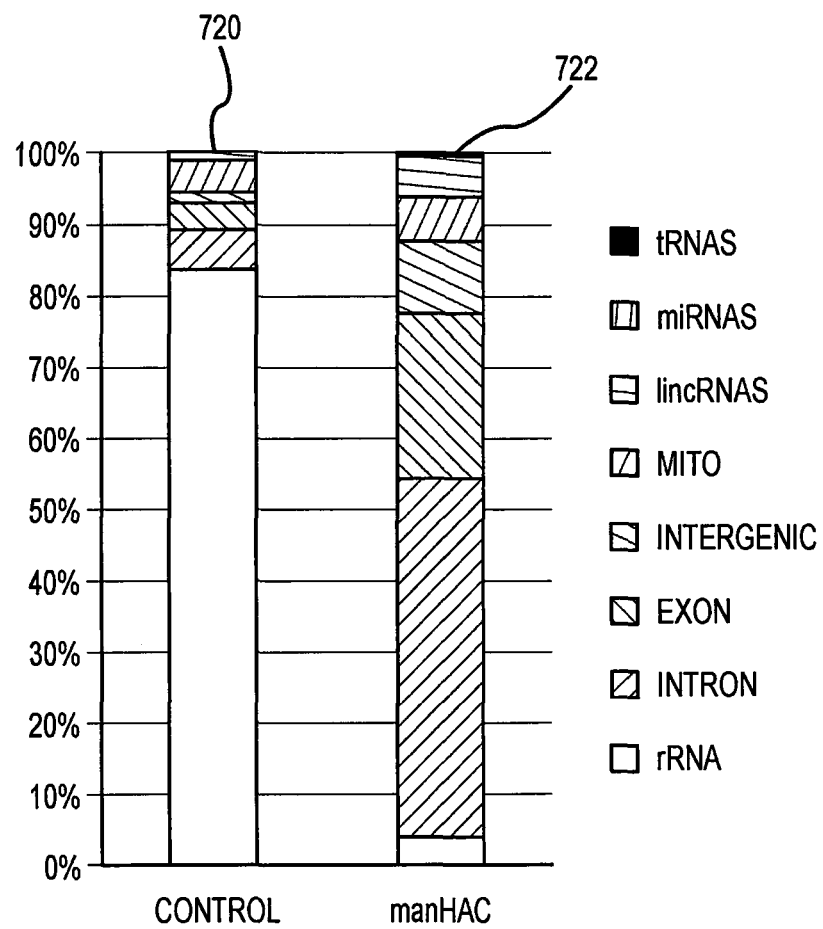
FIG. 12 is a bar graph illustrating performance of microfluidic HAC normalization on sequencing of human PBMC cell sample compared to control sample without normalization, according to one embodiment.

Referring to FIG. 12, another experiment, which demonstrated performance of microfluidic HAC normalization on sequencing of a human PBMC cell sample compared to a control sample without normalization. The longest band on the control bar 720 (over 80%) reflects the percentages of sequences that were from ribosomal RNA (uninformative, high abundance) before HAC normalization. The rRNA fraction on the HAC normalization bar 722 (e.g., the fractions after HAC normalization was performed on the sample) is less than 5% of the total. This experiment validated the ability of HAC normalization to greatly reduce rRNA in a nucleic acid sample.

Although specific embodiments of the invention have been described herein for purposes of illustration, various modifications may be made without deviating from the spirit and scope of the invention.

What is claimed is:

1. A system for enhancing a nucleic acid sample, the system comprising:
   at least one pump;
   at least one denaturing chamber;
   at least one microfluidic hydroxyapatite chromatography device configured for performing hydroxyapatite chromatography on the nucleic acid sample;
   at least one sample collector;
   one or more tubing fluidically connecting the at least one pump with the at least one denaturing chamber, the at least one microfluidic device, and the at least one sample collector such that the pump may be used to move the nucleic acid sample from the at least one denaturing chamber to the at least one microfluidic device and then to the at least one sample collector; and
   a first enclosure surrounding the at least one pump, the at least one denaturing chamber, and the at least one microfluidic device.

2. A system as in claim 1, further comprising a control unit coupled with the at least one pump to control its function.

3. A system as in claim 2, wherein the control unit is further coupled with at least one valve coupled with one of the one or more tubing to direct the nucleic acid sample in a desired direction within the system.

4. A system as in claim 1, wherein the at least one pump comprises:
   a buffer pump having a first volume;
   a sample pump having a second volume smaller than the first volume; and
   a tubing connecting the sample pump to the buffer pump.

5. A system as in claim 1, further comprising a conductivity detector disposed between the at least one microfluidic device and the at least one sample collector.

6. A system as in claim 1, wherein the at least one denaturing chamber comprises a heater comprising four or more reservoirs to accept four or more nucleic acid samples.

7. A system as in claim 6, wherein the at least one denaturing chamber comprises two heaters, each heater comprising a heater configured to accept four or more sample containers.

8. A system as in claim 7, wherein each of the heaters comprises:
   four or more microfluidic tubes, each tube configured to accept a PCR tube; and
   a thermal cover.

9. A system as in claim 1, wherein the at least one microfluidic device comprises a microfluidic bus configured to hold eight or more microfluidic columns.

10. A system as in claim 9, wherein the at least one microfluidic device comprises a removable ferrule for forming a seal with the eight or more microfluidic columns.

11. A system as in claim 1, further comprising:
   a first elution buffer chamber for holding a first elution buffer for eluting single stranded DNA; and
   a second elution buffer chamber for holding a second elution buffer for eluting double stranded DNA,
   wherein the first and second elution buffer chambers are each coupled with the one or more tubing, thereby fluidically connecting the first and second elution buffer chamber to the at least one pump, the at least one denaturing chamber, the at least one microfluidic device, and the at least one sample collector.

12. A system as in claim 1, further comprising a heater located in the first enclosure.

13. A system as in claim 1, further comprising a second enclosure surrounding the at least one sample collector.

14. A system as in claim 13, further comprising a cooling device located in the second enclosure.

15. A system for enhancing a nucleic acid sample, the system comprising:
   at least one pump;
   at least one denaturing chamber;
   at least one microfluidic hydroxyapatite chromatography device configured for performing hydroxyapatite chromatography on the nucleic acid sample;
   at least one sample collector;
   at least one elution buffer chamber;
   a first, multi-position valve coupled with the at least one pump, the at least one denaturing chamber, the at least one microfluidic device, and the at least one elution buffer chamber;
   a first tube connecting the at least one pump to the first valve;
   a second tube connecting the first valve with the at least one denaturing chamber;
   a second valve disposed on the second tube between the first valve and the at least one denaturing chamber;
   a third tube connecting the first valve and the at least one microfluidic device;
   a fourth tube connecting the first valve and the at least one elution buffer chamber;
   a fifth tube connecting the at least one microfluidic device and the at least one sample collector;
   a third valve disposed on the fifth tube between the at least one microfluidic device and the at least one sample collector; and
   a conductivity detector disposed between the at least one microfluidic device and the third valve.

16. A method for enriching a nucleic acid sample, the method comprising:
   denaturing the nucleic acid sample in a denaturing chamber;
   reducing a temperature in the denaturing chamber to allow the sample to at least partially reanneal;
   advancing the sample from the denaturing chamber into a microfluidic hydroxyapatite chromatography device, using a pump connected to the denaturing chamber and the microfluidic device via tubing;
   eluting single stranded DNA within the sample captured by the microfluidic device;
   monitoring, with a conductivity detector, output from the microfluidic device; and
   directing the eluted single stranded DNA into a sample collector.

17. A method as in claim 16, wherein the microfluidic device comprises a microfluidic bus that holds eight or more microfluidic hydroxyapatite chromatography columns, and wherein the method comprises enriching eight or more nucleic acid samples using the microfluidic bus.

18. A method as in claim 17, wherein the steps of denaturing and reducing the temperature are performed in two denaturing chambers comprising heaters, wherein each heater contains four or more of the nucleic acid samples.

19. A method as in claim 17, further comprising directing the eight or more nucleic acid samples into separate sample containers in the sample collector.

20. A method as in claim 17, further comprising directing the eight or more nucleic acid samples through a series of tubes connecting the denaturing chamber, the microfluidic device, the pump, and the sample collector.

21. A method as in claim 20, wherein directing the samples comprises adjusting at least one valve coupled with the series of tubes.

22. A method as in claim 16, further comprising controlling at least part of the method using a control device.

23. A method as in claim 16, further comprising:
   heating a first enclosure in which at least the denaturing chamber and the microfluidic device are housed; and
   cooling a second enclosure in which at least the sample collector is housed.

24. A method for enriching nucleic acid samples using a multiplexed, sample enriching system, the method comprising:
   denaturing multiple nucleic acid samples in at least one denaturing chamber of the system by raising a temperature in the at least one denaturing chamber to at least 95 degrees Celsius, wherein the samples are placed within reservoirs located in the at least one denaturing chamber;
   reducing the temperature in the at least one denaturing chamber for a sufficient period of time to allow a desired mixture of ssDNA and dsDNA to form;
   diluting the samples with buffer by pumping buffer into the reservoirs using a buffer pump of the system;
   drawing the samples out of the at least one denaturing chamber and into a holding tube of the system using a sample pump of the system;
   advancing the samples into separate columns of a multiplexed hydroxyapatite chromatography microfluidic device of the system, using the sample pump;
   advancing a single strand elution buffer through the microfluidic device to elute single stranded DNA within the samples and captured by the microfluidic device;
   monitoring, with a conductivity detector of the system, output from the microfluidic device; and
   directing the eluted single stranded DNA into separate sample collection chambers of a sample collection device, one chamber for each sample.

25. A method as in claim 24, further comprising, after advancing the samples into the columns:
filling the sample pump with fresh buffer; and
advancing the fresh buffer through the microfluidic device to flush out non-specifically bound sample.

26. A method as in claim 24, further comprising:
advancing a double strand elution buffer through the microfluidic device to elute double stranded DNA within the samples and captured by the microfluidic device;
monitoring, with a conductivity detector of the system, output from the microfluidic device; and
directing the eluted double stranded DNA into one or more separate chambers of the sample collection device.

27. A method as in claim 24, further comprising adjusting at least one valve of the system between at least two of the steps of the method, to direct the samples in a desired direction within the system.

28. A system for enhancing a nucleic acid sample, the system comprising:
at least one pump;
at least one denaturing chamber;
at least one microfluidic hydroxyapatite chromatography device configured for performing hydroxyapatite chromatography on the nucleic acid sample;
at least one sample collector;
one or more tubing fluidically connecting the at least one pump with the at least one denaturing chamber, the at least one microfluidic device, and the at least one sample collector such that the pump may be used to move the nucleic acid sample from the at least one denaturing chamber to the at least one microfluidic device and then to the at least one sample collector; and
a conductivity detector disposed between the at least one microfluidic device and the at least one sample collector.

29. A method for enriching a nucleic acid sample, the method comprising:
heating a first enclosure in which at least a denaturing chamber and a microfluidic hydroxyapatite chromatography device are housed;
cooling a second enclosure in which at least a sample collector is housed;
denaturing the nucleic acid sample in the denaturing chamber;
reducing a temperature in the denaturing chamber to allow the sample to at least partially reanneal;
advancing the sample from the denaturing chamber into the microfluidic device, using a pump connected to the denaturing chamber and the microfluidic device via tubing;
eluting single stranded DNA within the sample and captured by the microfluidic device; and
directing the eluted single stranded DNA into the sample collector.

* * * * *